United States Patent [19]

Tamm et al.

[11] 4,393,726
[45] Jul. 19, 1983

[54] SAMPLING VALVE USEFUL IN LIQUID CHROMATOGRAPHY

[75] Inventors: Rolf Tamm, Salem; Toma Tomoff, Uberlingen, both of Fed. Rep. of Germany

[73] Assignee: Bodenseeverk Perkin-Elmer & Co. GmbH, Fed. Rep. of Germany

[21] Appl. No.: 304,735

[22] Filed: Sep. 23, 1981

[30] Foreign Application Priority Data

Oct. 1, 1980 [DE] Fed. Rep. of Germany ....... 3037014

[51] Int. Cl.³ .......................................... G01N 35/00
[52] U.S. Cl. ................................. 73/864.84; 422/103
[58] Field of Search .......... 73/61.1 C, 863.71, 863.72, 73/863.73, 864.21, 864.81, 864.83, 864.84; 422/103

[56] References Cited

U.S. PATENT DOCUMENTS 3,961,534 6/1976 Gundelfinger .
4,068,528 1/1978 Gundelfinger .
4,182,184 1/1980 Bakalyar .
4,242,909 1/1981 Gundelfinger .

OTHER PUBLICATIONS

Operating Instructions for Model 7125 Syringe Loading Sample Injector, Rheodyne Inc., Box 966, Cotati, Calif. 94928, 9/80, 6 pages.
Model 7125 Syringe Loading Sample Injector Bulletin 106, Rheodyne Inc., Box 996, Cotati, Calif. 94928, 2/81, 4 pages.

Primary Examiner—S. Clement Swisher
Attorney, Agent, or Firm—S. A. Giarratana; F. L. Masselle; R. A. Hays

[57] ABSTRACT

A sampling valve useful in liquid chromatography includes a stationary valve member and a valve member movable with respect thereto. The movable valve member includes an axial bore having a cross-section permitting the insertion therethrough of a sample injection needle.

3 Claims, 6 Drawing Figures

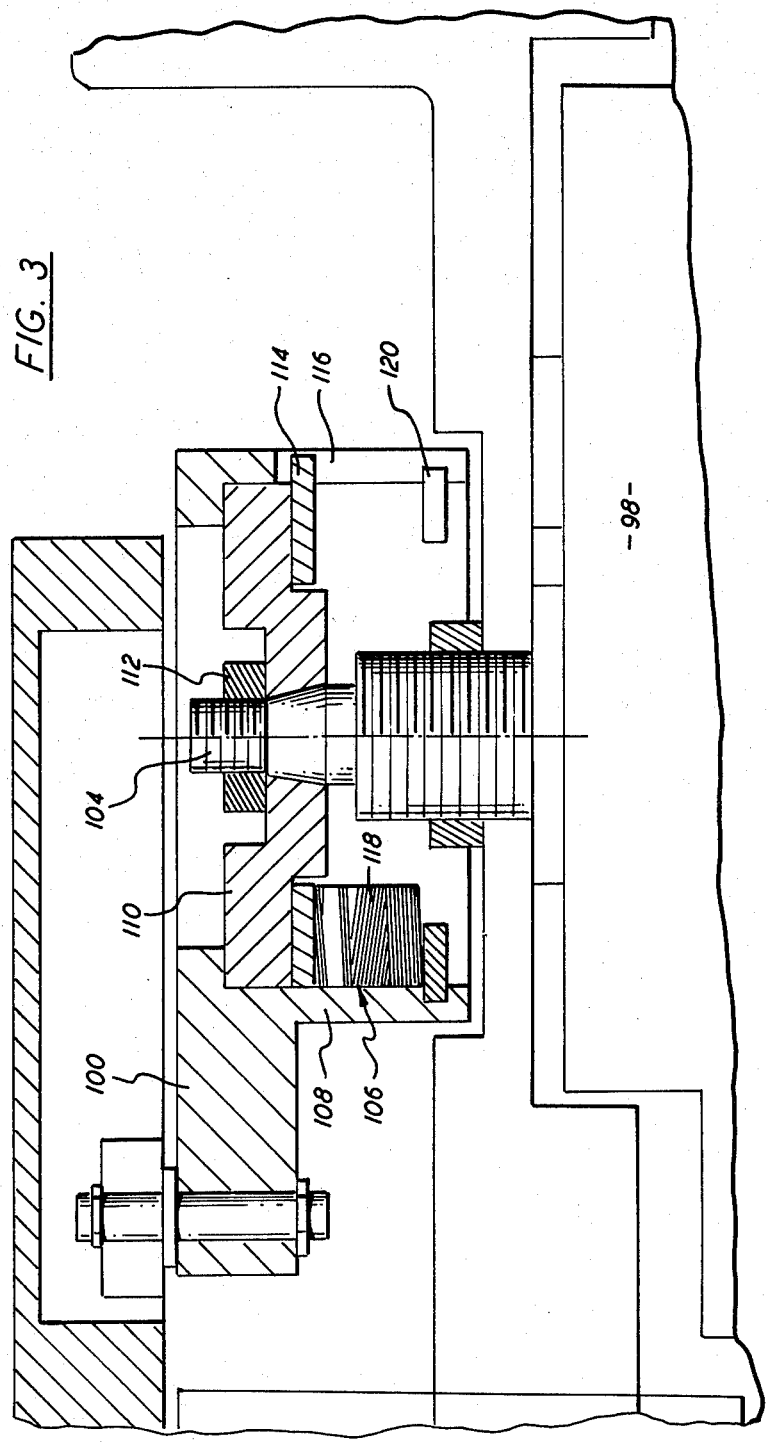

SAMPLING VALVE USEFUL IN LIQUID CHROMATOGRAPHY

BACKGROUND OF THE INVENTION

The present invention generally relates to a sampling valve useful in liquid chromatography and, in particular, relates to such a valve having a dosing bore adapted to accept an injection needle.

In a prior art sample inlet valve, for example that described in the brochure, "Operating Instructions for Model 7125 Syringe Loading Sample Injector" of Rheodyne Incorporated, Berkley, California, a stationary stator and a rotor rotatable relative thereto are provided. In use, an injection needle is inserted into the rotor to contact the surface of the stator, which needle does not enter the stator beyond the contact surface. The dosing bore in the stator having a smaller diameter than the injection needle, whereby such entry is prevented. After the sample has been delivered into the dosing bore, the rotor is rotated to change the sample inlet valve over. The rotation takes place while the injection needle remains in its position in the rotor. If the injection needle were to be withdrawn prior to the changing of the sample inlet valve, sample fluid would be sucked from the stator into the rotor via the plunger action of the injection needle. This sample quantity sucked into the rotor would cause cross-contamination.

Another difficulty encountered in prior art valves is that the changing of the rotor results in the end of the injection needle scratching the contact surface of the stator. This results in undesirable wear and necessitates the use of particularly hardened contact surfaces.

It is also necessary, in prior art valves, to utilize an injection needle which is provided with a flush end, the tip of which then sealingly engages the contact surface. Thus, in the prior art, it is not feasible to use pointed injection needles. The use of such needles would further increase the wear of the contact surface. Further, if a pointed needle were used, liquid would undoubtedly remain in the rotor-side bore, into which the injection needle is inserted. This would also result in cross-contamination.

SUMMARY OF THE INVENTION

Based on the above, it is one object of the present invention to develop a valve for feeding samples in liquid chromatography, such that the wear of the contact surface on the stator is reduced and the risk of cross-contamination is avoided.

This object is achieved, at least in part, by providing a valve wherein the dosing bore is adapted to accept the injection needle. In use, an air volume into the injection needle prior to the sucking-in of the sample liquid, the front tip of the injection needle, for the purpose of directing the sample into the dosing loop as inserted through a bore of the movable valve member and into a dosing bore of the stationary valve member, retracting the injection needle after the sample has been introduced and prior to the changing over of the sample inlet valve.

In the method used with the present inventive valve, the air, which had been sucked in prior to the sample liquid, is injected into the stationary valve member and into the adjacent end of the dosing loop, after the sample liquid has been fed into the stationary valve member. This air cushion, rather than sample liquid, is adjacent the injection needle so that when the injection needle is retracted, the piston action of the injection needle does not suck sample liquid back into the movable valve member. The sample liquid thus remains safely within the stationary valve member or within the dosing loop. Thus, it is possible to insert the end of the needle into the stationary valve member whereby sample liquid cannot get between the contact surface and the sealing surface, respectively, of the valve members, In addition, the injection needle can safely be withdrawn prior to the changing over of the valve, whereby the injection needle neither wears the contact surface nor impedes the changing-over movement.

Other objects and advantages will become apparent to those skilled in the art from the following detailed description of the invention and the accompanying drawing.

BRIEF DESCRIPTION OF THE DRAWING

The drawing, not drawn to scale, comprises:

FIG. 3: is a partial sectional view of an actuating device for the sample inlet valve;

DETAILED DESCRIPTION OF THE INVENTION

Figure 1:
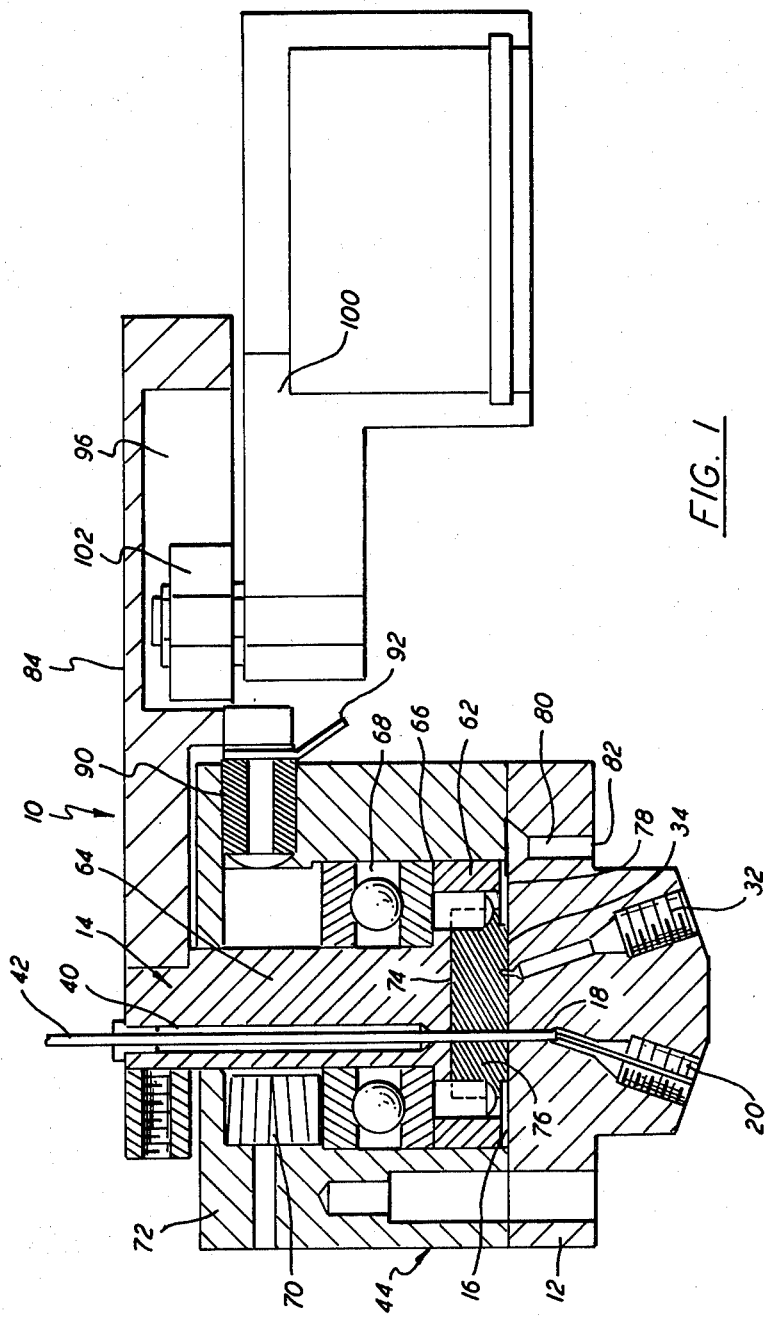
FIG. 1: which is a sectional view of a sample inlet valve embodying the principles of the present invention and adapted for use in liquid chromatography.
Figure 2:
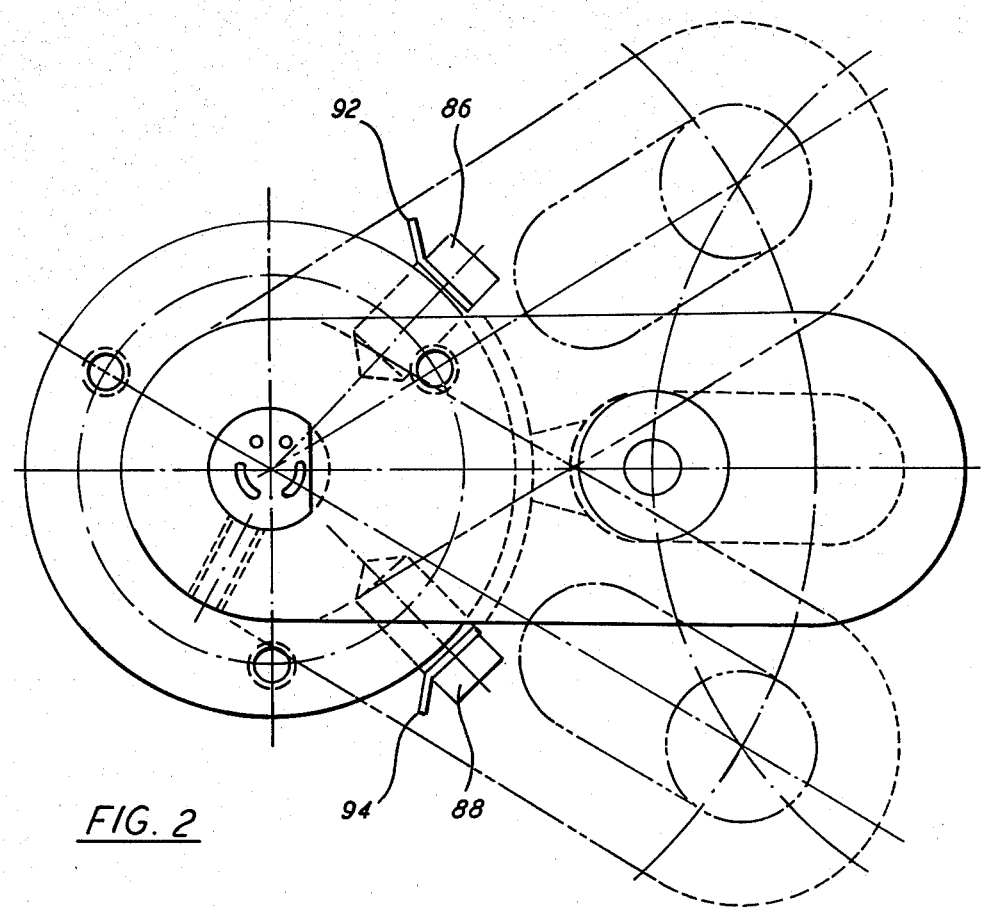
FIG. 2: is a plane view of the valve shown in FIG. 1.

FIGS. 1 and 2 illustrate a sample inlet valve 10 having a stationary valve member 12 and a valve member 14 movable relative to the stationary valve member 12. The stationary valve member 12 includes a flat contact surface 16, having a dosing bore 18 therein, communicating with a port 20 for connection to one end of a dosing loop 22. The stationary valve member 12 further includes bores which communicate with ports 24, 26, 28, 30, 32 for connection to a transport liquid source which is usually a transport liquid pump, a separating column, outlets and the other end of the dosing loop 22, respectively. The valve member 14, movable relative to the stationary valve member 12 abuts, with a sealing surface 34, the contact surface 16 of the stationary valve member 12. The member 14 contains connecting passages 36 and 38 arranged to connect the bores of the stationary valve member 12 such that, in a first operative position of the movable valve member 14, the bore to be connected to the transport liquid source communicates with the bore to be connected to the separating column, and the bore to be connected to the other end of the dosing loop 22 communicates with a bore which is connected to an outlet. In a second operative position of the movable valve member 14, the bore to be connected to the transport liquid source communicates with the bore to be connected to said other end of the dosing loop 22, and the bore to be connected to said one end of the dosing loop 22 communicates with the bore to be connected to the separating column. An axial bore 40, for sealingly inserting an injection needle 42, is provided in the movable valve member 14, the axial bore 40, in the first operative position, is aligned with the dosing bore 18 of the stationary valve member 12.

The stationary valve member 12 is, in one embodiment, the bottom portion of a pot-shaped valve body 44. The movable valve member 14 is a rotor which abuts, with a sealing surface 34, the bottom of the valve body 44 forming the contact surface 16. As can be seen best from FIGS. 4 and 5, the bores 46, 48, 50, 18, 54 and 56, which are arranged to be connected to the other end of the dosing loop 22, to the transport liquid source, to said one end of the dosing liquid loop 22 as well as to first and second outlets 58, 60, respectively, terminate in the bottom of the valve body 44. Preferably, the bores lie in a circle and angularly spaced apart from each other by 60°. Two arcuate connecting passages 36 and 38 are provided in the sealing surface 34 of the rotor 14, and extend through arcs of about 60° each and are angularly spaced apart by 60°. The axial bore 40 for inserting the injection needle 42 is angularly spaced by 60° relative to one of the connecting passages 38.

The rotor 14 includes a disc-shaped head portion 62 engaging the bottom of the valve body 44, and a central shaft 64, whereby an annular shoulder 66 is formed around the shaft 64 on the side remote from the sealing surface 34. A thrust bearing 68 in the form of an axial ball bearing is located on the annular shoulder 60. Biased, annular spring plates 70 are arranged around the shaft 64 between the thrust bearing 68 and an annular housing cover 72 surrounding the shaft 64. The head portion 62 has a central, shallow recess in its end face facing the contact surface 16. A disc-shaped plastic body 76 forming the sealing surface 34 is affixed in the recess 64. The plastic body 76 is stepped axially around the sealing surface 34, whereby an annular chamber 78 is formed surrounding the sealing surface 34 and contact surface 16 and the circumferential wall of the valve body 44. The annular chamber 78 communicates with an outlet 82 via a leakage bore 80 extending through the bottom portion of the valve body 44.

A change-over lever 84 is attached to the shaft 64 of the rotor 14 and is movable between two stops 86 and 88 (see FIG. 2), which can be provided on the valve body 44. When the change-over lever 84 engages the stop 86, the rotor 12 is in its first operative position and when the change-over lever 84 engages the other stop 88, the rotor 14 is in its second operative position. As can best be seen in FIG. 1, the stops, 86 and 88, are attached to the valve body 44 through electrically insulating bodies 90. The stops, 86, 88, and change-over lever 84 serve as switch contacts in a circuit controlling the operative positions of the rotor 14. The circuit is preferably arranged to automatically initiate the steps provided by a preselected program, for example, after a certain operative position has been attained. To this end, the stops, 86 and 88 are provided with connector lugs.

The change-over lever 84, in one embodiment, has a longitudinal groove 96. A reversible servomotor 98 (FIG. 3), the axis of which is parallel to the axis of rotation of the rotor 14, carries a driving lever 100, which engages, for example, by means of an engaging roller the longitudinal groove 96 of the change-over lever 84. As can be seen from FIG. 3, the driving lever 100 is connected through a slipping clutch 106 to the shaft 104 of the electric motor serving as servomotor 98. Preferably, a cylindrical housing part 108 is provided on the driving lever 100. A plate 110 is attached to the shaft 104 of the servomotor 98 by means of a nut 112. A clutch ring 114 engages the plate 110 and is guided axially but non-rotatably within the cylindrical housing part 108 by guide means. The clutch ring 114 is held in engagement with the plate 110 by spring discs 118 supported on an abutment ring 120. Thus, the slipping clutch yields, when the change-over lever 84 engages one of the stops 86 and 88.

The sample inlet valve 10 illustrated in FIG. 1 has a dosing bore 18 having a cross-section permitting insertion therethrough of the injection needle 42.

Figure 6:
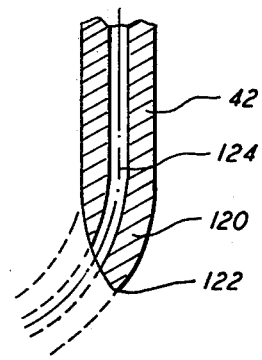
FIG. 6: shows the tip of an injection needle.

As can be seen from FIG. 1 and in particular from FIG. 6, the injection needle 42 is provided with a pointed end 120 having a tip 122. In the preferred embodiment, the pointed end 120 of the injection needle 42 has been formed by laterally bending a capillary, as shown in broken lines in FIG. 6. As a result, the longitudinal passage 124 of the capillary is cut-off substantially on its longitudinal axis and a longitudinal passage 124 deflected at its end and opening laterally.

Figure 4:
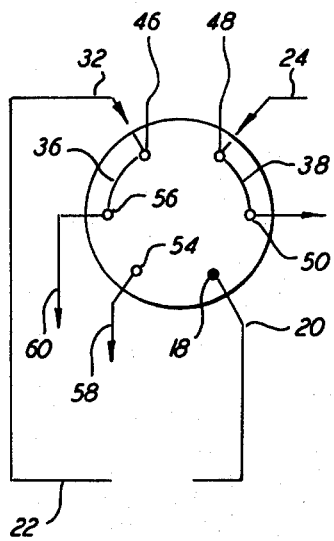
FIG. 4: depicts the sample inlet valve in a first operative position.

In one mode of operation a sample is introduced into the dosing loop 22 by means of the injection needle 42 through the sample inlet valve 10 with the stationary valve member 12 and the movable valve member 14 in the first operative position thereof. This operative position is shown in FIG. 4. Subsequently, the sample inlet valve 10 is changed over to the second operative position, in which it connects a transport liquid source, the dosing loops 22 and a separating column in series. Prior to the sucking-in of the sample liquid, an air volume is sucked into the injection needle 42. To introduce the sample into the dosing loop 22, the injection needle 42 is inserted through the bore 40 of member 14, down to the dosing bore 18 into the stationary valve member 12. Thus the sample liquid emerges from the injection needle 42 only in the stationary valve member 12 downstream of both the sealing surface 34 and the contact surface 16. After the sample has been introduced and prior to the changing-over of the sample inlet valve 10, the injection needle 42 is withdrawn. No sample liquid is sucked back into the bore 40 due to the plunger action of the injection needle 42 during removal thereof because of the air-volume. The air-volume, which has been sucked in prior to the sample liquid has also been urged into the dosing bore 18, after the sample liquid has been dispensed.

Insertion of the injection needle 42 into the stationary valve member 12 and beyond the sealing surface 34 thereof also permits the use of an injection needle 42 having a pointed end 120, as, for example, illustrated in FIG. 6. Even if a pointed injection needle 42 is used, no sample liquid is retained in the bore 40 of the movable valve member 14, as would be the case, if an injection needle having a pointed end were used with a prior art sample inlet valve.

Preferably, an injection needle 42 as shown in FIG. 6 is used, which needle 42 has been made by lateral bending of the end of a capillary and oblique cutting-off of this bent end whereby the resultant injection needle 42 has a tip 122 substantially on its longitudinal axis and a longitudinal passage 124 deflected at its end and opening laterally. In detail, the first operative position is illustrated in FIG. 4. The passage 40 communicates with the dosing bore 18 and, through port 20, with the dosing loop 22. The other end of the dosing loop 22 is connected to an outlet through port 32, bore 46, connecting passage 36 and bore 56. The transport liquid source, usually a transport liquid pump, is connected to the separating column via port 24, bore 48, connecting passage 38 and bore 50 as well as port 26. Hence, sample liquid from the injection needle 42 can be dispensed into the dosing loop 22. Upon withdrawal, air but no sample liquid sucked into the bore 40 of the movable valve member 14 due to the plunger action of the injection needle 42. Thus, cross-contamination is substantially completely avoided.

Figure 5:
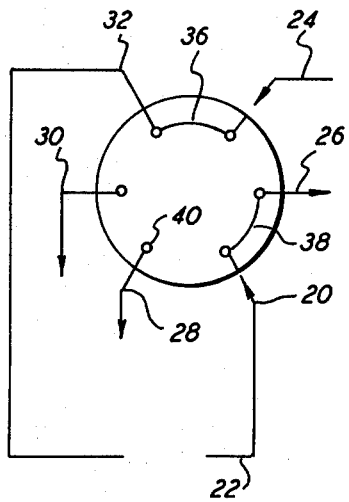
FIG. 5: depicts the sample inlet valve in a second operative position.

After sample injection the sample inlet valve 10 is moved to its second operative position, as illustrated in FIG. 5. Now the transport liquid source, the dosing loop 22 and the separating column are connected in series, the transport liquid flowing from port 24 through bore 48, connecting passage 36, bore 46, port 32, the dosing loop 22, port 20, bore 18, connecting passage 38 bore 50 and port 26 through the separating column. Hence, the entire uncontaminated sample is provided to the column for accurate analysis.

The sample inlet valve 10 may be actuated manually by means of the change-over lever 84. It may, however, also be changed over by the servomotor 98, as illustrated, whereby sample feeding may be automated.

Although the present invention has been described herein in relation to a specific embodiment it will be understood that it is for exemplary purposes only and is not deemed to be limiting. The present invention is limited only by the appended claims and the reasonable interpretation thereof.

What is claimed is:

1. Method of feeding samples in liquid chromatography, said method comprises the steps of:

providing a sample into a dosing loop by means of an injection needle through a sample inlet valve said valve having stationary and movable members in a first position of said valve, changing said sample valve to a second position, thereby connecting, in series, a transport liquid source, said dosing loop and a separating column, and wherein said providing step includes:

sucking an air volume into said injection needle prior to sucking-in said sample;

inserting said injection needle, through a bore in said movable valve member into a dosing bore of said stationary valve member, retracting said injection needle after the sample has been introduced and prior to said changing-over of said sample valve.

2. Method as claimed in claim 1, wherein an injection needle having a pointed tip is used.

3. Method as claimed in claim 2, wherein the use of an injection needle which has been made by lateral bending of the end of a capillary and oblique cutting off of this bend end, whereby the injection needle which has been made by lateral bending of the end of a capillary and oblique cutting off of this bend end, whereby the injection needle has a tip substantially omits longitudinal axis and a longitudinal passage deflected at its end and opening laterally.

* * * * *